United States Patent [19]

Murphy et al.

[11] Patent Number: 5,561,099
[45] Date of Patent: Oct. 1, 1996

[54] ALKYLSILOXANES AS ADJUVANTS FOR AGRICULTURE

[75] Inventors: Gerald J. Murphy, Hopewell Junction; George A. Policello, Peekskill, both of N.Y.

[73] Assignee: OSi Specialties, Inc., Danbury, Conn.

[21] Appl. No.: 135,916

[22] Filed: Oct. 13, 1993

[51] Int. Cl.$^6$ .......................... A01N 55/10; C09K 17/38
[52] U.S. Cl. ................ 504/116; 71/DIG. 1; 504/193; 106/287.14; 252/174.15; 514/63
[58] Field of Search ................... 504/193, 116; 71/DIG. 1; 106/287.1, 287.13, 287.14, 287.15, 284.16; 252/174.15; 514/63

[56] References Cited

U.S. PATENT DOCUMENTS

| | | | |
|---|---|---|---|
| 3,299,112 | 1/1967 | Bailey | 504/193 |
| 4,155,995 | 3/1979 | Heinz et al. | 424/184 |
| 4,171,267 | 10/1979 | McAfee et al. | 252/8.6 |
| 4,337,166 | 6/1982 | Hill et al. | 252/174.15 |
| 4,514,319 | 4/1985 | Kulkarni et al. | 252/321 |
| 4,654,328 | 3/1987 | Itoh et al. | 514/63 |
| 5,045,225 | 9/1991 | Aronson et al. | 252/174.15 |
| 5,104,647 | 4/1992 | Policello | 514/772 |
| 5,145,879 | 9/1992 | Budnik et al. | 521/112 |

FOREIGN PATENT DOCUMENTS 0121210 10/1984 European Pat. Off. .

OTHER PUBLICATIONS

Chemical Abstract; vol. 116, 1992; p. 436.
Organosilicone Surfactants As Adjuvants For Agrochemicals; Peter JG Stevens; pp. 103–122 (1993).
Modeling the Foliar Behavior of Atrazine with and without Crop Oil Concentrate on Giant Foxtail and the Effect of Tripiphane on the Model Rate Constants, P. McCall et al, J. Agric. Food Chem 1986, 34, 235–238.
Silicones, Chemistry & Technology, CRC Press, 1991, pp. 1–6.

*Primary Examiner*—Jos3 G. Dees
*Assistant Examiner*—B. Bembeuick
*Attorney, Agent, or Firm*—Donald T. Black

[57] ABSTRACT

Linear alkylsilicone compounds of the formula

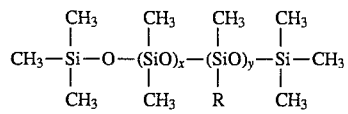

wherein x=0 to 20, preferably 0 to 10, most preferably 0 to 1; y=1 to 10, preferably 1 to 5, most preferably 1; and R is an alkyl or alkyl ester group containing 6 to 16 carbons, or cyclic alkylsilicone compounds of the formula

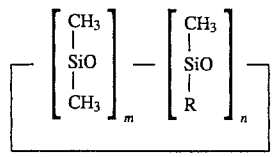

where m is 0 to 4, preferably 0 to 2, most preferably 0, and n is 1 to 5, preferably 3 to 5, most preferably 4, provided that m+n=3 to 5,
are adjuvants for agricultural applications of oil-containing compositions. Especially preferred alkylsilicone compounds have a degree of polymerization of ≦6 and an alkyl content of ≦50% by weight. The compounds potentiate spreading of mineral or vegetable oils or oil-containing emulsions in dormant spray oils, crop oil concentrates, pesticides, and the like on difficult-to wet surfaces such as waxy leaf cuticles and arthropod exoskeletons.

5 Claims, No Drawings

ALKYLSILOXANES AS ADJUVANTS FOR AGRICULTURE

DESCRIPTION

1. Technical Field

The present invention relates to blends of oil such as mineral oil or vegetable oil with alkyl-modified silicones (AMS) that are useful as adjuvants for agricultural applications.

Many useful oil-based agricultural chemicals are less effective than desired because they don't spread well. It is typical to apply oil-based chemicals using a carrier such as a mineral or vegetable oil, or to apply dormant oils as aqueous sprays. The bulk surface tension of a liquid plays a key role in its ability to spread on hydrophobic surfaces such as a waxy leaf cuticle or an arthropod exoskeleton. If the surface tension of a liquid such as an unmodified mineral or vegetable oil is not sufficiently low, the droplet will not effectively spread. There is a need for adjuvants which reduce the surface tension of lipophilic liquids and, thereby, increase the effectiveness of oil-based agricultural chemicals.

2. Background of the Invention

The use of oils as adjuvants or carriers for agricultural applications is well known. Petroleum and vegetable oils have been used in formulations for dormant spray oils, in preparations for the management of insects and mites including those that suffocate arthropod pests by clogging their spiracles, in crop oil concentrates and crop oils, and in emulsifiable concentrates. One of the effects of the oil is to increase the penetration of pesticides into the target organism. In addition, the oils enhance spreading on target surfaces, which increases coverage.

According to P. J. McCall, et al. (*J. Agric. Food Chem.*, 34(2), 235–8), the addition of a crop oil concentrate (COC) to atrazine spray solutions significantly increased the amount of pesticide absorbed by giant foxtails sprayed with the chemical. Typically, 30% of the applied chemical penetrated the leaf in the presence of COC, while only 10% penetrated without COC.

Kulkarni, et al. (U.S. Pat No. 4,514,319) disclosed relatively high molecular weight alkyl-modified silicones that, when used in connection with organo-silicone surfactants, reduced the surface tension of hydrocarbon oils containing hydrophobic fillers, thus providing high efficiency antifoam compositions.

In U.S. Pat. No. 5,045,225, Aronson, et al., disclosed the use of alkylaminosilicones that were soluble in mineral oil and resulted in enhanced surface activity. The compounds imparted self-hydrophobing properties to antifoam compositions containing hydrophilic mineral particles such as silica.

McAfee, et al. (U.S. Pat. No. 4,171,267) disclosed an organopolysiloxane fluid as a component of a miscible composition for lubricating organic fibers that contained a hydrocarbon oil and a bridging agent obtained by reacting an organopolysiloxane with a long chain alcohol.

SUMMARY OF THE INVENTION

It is an object of this invention to provide an alkyl-modified silicone/carrier oil composition that gives improved spreading properties relative to the carrier oil alone.

It is another object of this invention to provide an alkyl-modified silicone/carrier oil composition that exhibits lower nonaqueous surface tension values than the carrier oil alone.

It is a further object of this invention to provide a homogeneous composition that gives increased foam control relative to formulations based on the carrier oil alone.

Still another object of this invention is to provide a crop oil concentrate composition containing an alkyl-modified silicone spreading agent.

These and other objects are accomplished by the present invention which provides, as adjuvants for oil-containing compositions, especially agricultural compositions, linear alkylsilicone compounds of the formula 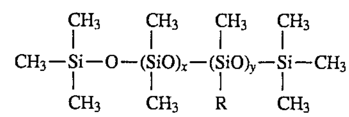 wherein x=0 to 20, preferably 0 to 10, most preferably 0 to 1 and y=1 to 10, preferably 1 to 5, most preferably 1. R is a branched or linear alkyl or alkyl ester group containing 6 to 18 carbons, preferably a linear alkyl containing from 8 to 14 carbon atoms, more preferably from 8 to 12 carbon atoms. R may be the same or different on any given molecule.

The invention also provides cyclic alkylsilicone compounds of the formula where m is 0 to 4, preferably 0 to 2, most preferably 0 to 1, and n is 1 to 5, preferably 3 to 5, most preferably 4 to 5, provided that m+n=3 to 5, and R is as defined above.

Preferred linear alkylsilicone compounds have a degree of polymerization of ≦6 and an alkyl content of ≦50% by weight. Preferred cyclic alkylsilicone compounds have a degree of polymerization of ≦5 an an alkyl content of ≦50% by weight.

Novel oil-based agricultural adjuvant compositions comprise a mixture of about 1% to about 99% by weight of a linear or cyclic alkyl-modified silicone, or a mixture thereof, and from about 99% to about 1% by weight of an oil carrier such as paraffinic or aromatic-based mineral oils, or animal or vegetable oils, e.g., soybean oil, canola oil, olive oil, corn oil, cotton seed, sesame seed oil and the like. Methylated oils, such as methylated soybean oil, methyl palmitate, methyl oleate, and the like, may also be employed, or mixtures of oils. In preferred embodiments, oil-based compositions containing an alkyl-modified silicone exhibit improved spreading properties.

Many compositions of the invention contain a pesticide such as herbicides, fungicides and insecticides, or mixtures thereof. Example pesticides include growth regulators, photosynthesis inhibitors, pigment inhibitors, mitotic disruptors, amino acid synthesis inhibitors, lipid biosynthesis inhibitors, cell wall inhibitors and cell membrane disruptors.

Optionally, the composition can include from 0.1 to 2.5 wt % of a hydrophobized silica filler, such as Tullenox® 500. The composition may also include a nonionic surfactant that is present from about 1% to about 50% by weight. The nonionic surfactant is selected from a group of surfactants that are soluble in the alkyl-modified silicone/carrier oil matrix, and having an HLB between about 8 and 17.

The invention also provides methods for using the alkylsilicone and oil compositions, particularly in combination with pesticides.

DETAILED DESCRIPTION OF THE INVENTION

In accordance with the present invention there is provided an oil-based agricultural adjuvant, which comprises an organosilicone compound and a carrier oil. The compositions can optionally contain pesticides, fillers and/or surfactants.

Linear organosilicone compounds of the invention include alkyl-modified silicones (AMS) having the general formula:

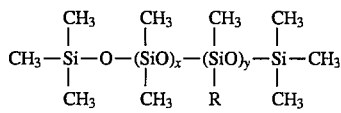

wherein x=0 to 20, preferably 0 to 10, most preferably 0 to 1 and y=1 to 10, preferably 1 to 5, most preferably 1. R is a branched or linear alkyl or alkyl ester group containing 6 to 18 carbons, preferably a linear alkyl containing from 8 to 14 carbon atoms, more preferably from 8 to 12 carbon atoms. R may be the same or different on any given molecule.

Cyclic organosilicone compounds of the invention include alkyl-modified silicones of the formula

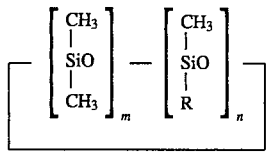

where m is 0 to 4, preferably 0 to 2, most preferably 0, and n is 1 to 5, preferably 3 to 5, most preferably 4 to 5, provided that m+n=3 to 5, and R is as defined above.

The preferred linear compounds have a degree of polymerization (DP) of $\leq 12$, most preferably a DP of $\leq 6$, and an alkyl content of $\leq 50\%$ by weight. For linear structures, the DP is defined as the total value of x+y+2, which represents the number of siloxane units in the silicone copolymer plus two end groups. For linear compounds, the weight percent (denoted below as WT %) alkyl is defined as:

$$\text{Wt \% Alkyl} = \frac{(\text{MW alkyl})(y)}{162.38 + [74.15x + y(60.13 + \text{MW Alkyl})]} \times 100$$

Cyclic structures have DP=x+y, and the DP$\leq 5$. For cyclic alkylsilicone compounds the weight percent alkyl is defined as:

$$\text{Wt \% Alkyl} = \frac{(\text{MW alkyl})(y)}{74.15x + y(60.13 + \text{MW Alkyl})} \times 100$$

where MW is the molecular weight of the alkyl group.

The carrier oil of the invention is comprised of oils and mixtures thereof, selected from paraffinic, isoparaffinic and cycloparaffinic mineral oils, vegetable oils, such as soybean oil, canola oil, castor oil, palm oil, olive oil, corn oil, cotton seed, sesame seed oil and the like. In addition, methylated oils, such as methylated soybean oil, methyl palmitate, methyl oleate, and the like are also suitable carrier oils. Mixtures of mineral, vegetable and/or methylated oils may also be employed.

Example mineral oils are those marketed under the trade names EXXOL®, ISOPAR®, NORPAR® and Orchex® from Exxon Chemical Houston, Tex. Methylated oils such as the methylated soybean oil are available from Henkle, Canada, under the product name "emery 2235, Distilled Methylsoyate". These carrier oils are only given as examples and are not intended to limit the scope of this invention, since one skilled in the art would be able to determine other suitable oils from this listing.

The agricultural composition of this invention is typically comprised of a mixture of an alkyl-modified silicone (AMS) that is oil-soluble or dispersible, and a suitable carrier oil. The AMS component consists of from about 1% to about 50% by weight of the composition, having a degree of polymerization (DP) of $\leq 25$, and an alkyl content of $\leq 50$ Wt %. The carrier oil is present from about 50% to about 99% by weight of the composition.

Optionally, the composition can include from about 0.1% to about 2.5% by weight of a hydrophobized silica filler, for example, Tullenox® 500 (Tulco), and Aerosil® R-812 (Degussa). The composition may also include a nonionic surfactant that is present from about 1 to about 50% by weight. The nonionic surfactant is selected from a group of surfactants that are soluble in the AMS/carrier oil matrix, and having an HLB between 8 and 17.

When the composition contains the optional ingredients, the AMS/carrier oil mixture makes up the balance of the composition, with the ratio of the AMS/carrier oil portion 99:1 to 1:99.

The composition is prepared by combining the components in a desired ratio, consistent with the guidelines described above, and mixing these ingredients according to conventional methods that will provide a clear to slightly hazy, uniform product. Mixing by a mechanical agitator or a mechanical shaker are examples of such methods. When the optional filler is included in the composition the ingredients are combined using a high shear mixer, such as a Lightnin' mixer.

The alkylsilicone of this invention promotes the spreading of the carrier oil on plant and/or arthropod surfaces. The alkylsilicone is useful as a spreading agent for oil-based adjuvants such as crop oil concentrates, dormant oils, and non-aqueous, ultra-low volume oil sprays, where the pesticide is dispersed or dissolved in the carrier oil. In addition, the alkylsilicones of the present invention are useful as spreading agents when incorporated into oil-based pesticide formulations, such as emulsifiable concentrates.

By "pesticide" is meant any compound used to destroy pests, including herbicides, fungicides, insecticides, rodenticides and the like. The term specifically includes oily materials not otherwise toxic but nevertheless used as pesticides in the destruction of aphids, scale insects, and the like by suffocation (e.g., by clogging their spiracles). Illustrative examples of pesticides which can be employed in the present invention include, but are not limited to, growth regulators, photosynthesis inhibitors, pigment inhibitors, mitotic disruptors, lipid biosynthesis inhibitors, cell wall inhibitors, and cell membrane disruptors. The amount of pesticide employed in compositions of the invention varies with the type of pesticide employed.

The following are representative, but nonlimiting examples of pesticide compounds that can be used in the compositions of the invention:

Growth Regulators

Phenoxy Acetic Acids, such as 2,4-D: 2,4-dichlorophenoxyacetic acid

Phenoxy Propionic Acids, such as Dichlorprop: (RS)-2-(2, 4-dichloropenoxy) propionic acid Mecoprop: (RS)-2-(4-chloro-o-tolyloxy)-propionic acid Phenoxy Butyric Acids, such as 2,4-DB: 4-(2,4-dichlorophenoxy)butyric acid Benzoic Acids, such as Dicamba: 3,6-dichloro-o-anisic (I)

Fluroxypyr: 4-amino-3,5-dichloro-6-fluoro-2-pyridyloxyacetic acid

Picloram: 4-amino-3,5,6-trichloropyridine-2-carboxylic acid; 4-amino-3,5,6-trichloropicolinic acid Triclopyr: 3,5,6-trichloro-2-pyridyloxyacetic acid Copyralid: 3,6-dichloropyridine-2-carboxylic acid

Photosynthesis Inhibitors

Triazines and s-Triazines such as Hexazinone: 3-cyclohexyl-6-dimethylamino-1-methyl-1,3,5-triazine-2,4(1H,3H)-dione Metribuzin: 4-amino-6-tert-butyl-3-methylthio-1,2,3-triazine-5(4H)-one Atrazine: 6-chloro-$N^2$-ethyl-$N^4$-isopropyl-1,3,5-triazine-2,4-diamine Simazine: 6-chloro-$N^2,N^4$-diethyl-1,3,5-triazine-2,4-diamine Cyanazine: 2-(4-chloro-6-ethylamino-1,3,5-triazin-2-ylamino)-2 methylpropionitrile Prometon: $N^2,N^24$-di-isopropyl-6-methoxy-1,3,5-triazine-2,4,diamime Ametryn: $N^2$-ethyl-$N^4$-isopropyl-6-methylthio-1,3,5-triazine-2,4-diamine Substituted ureas, such as Diuron: 3-(3,4-dichlorophenyl)-1,1-dimethylurea (I)

Fluometuron: 1,1-dimethyl-3-(a,a,a-trifluoro-m-tolyl)urea (I)

Linuron: 3-(3,4-dichlorophenyl)-1-methoxy-1-methylurea(I)

Tebuthiuron: 1-(5-tert-butyl,1,3,4-thiadiazol-2-yl)-1,3-dimethylurea (I)

Uracils, such as Bromacil: 5-bromo-3-sec-butyl-6-methyluracil (I)

Terbacil: 3-tert-butyl-5-chloro-6-methlyuracil (I)

Other photosynthesis inhibitors, such as Bentazon: 3-isopropyl-1H-2,1,3-benzothiadiazin-4(3H)-one 2,2-dioxide (I)

Desmedipham: ethyl 3'-phenylcarbamoyloxycarbanilate; ethyl 3-phenylcarbamoyloxyphenylcarbamate; 3-ethoxycarbonylaminophenyl phenylcarbamate Methazole: 2-(3,4-dichlorophenyl)-4-methyl-1,2,4-oxadiazolidine-3,5-dione (I)

Phenmedipham: methyl 3-(3-methylcarbaniloyloxy)carbanilate; 3-methoxycarbonylaminophenyl 3'-methylcarbanilate Propanil: 3',4'-dichloropropionanilide (I)

Pyridate: 6-chloro-3-phenylpyridazin-4-yl S-octlyl thiocarbonate

Pigment Inhibitors

Amitrole: 1H-1,2,4-triazol-3-ylamine; 3-amino-1H-1,2,4-triazole

Clomazone: 2-(2-chlorobenzyl)-4,4-dimethyl-1,2-oxazolidin-3-one; 2-(2-chlorobenzyl)-4,4-dimethylisoxazolidin-3-one Fluridone: 1-methyl-3-phenyl-5-(a,a,a-trifluoro-m-tolyl)-4-pyridone Norflurazone: 4-chloro-5-methylamino-2-(a,a,a-trifluoro-m-tolyl)pyridazin-3(2H)-one

Mitotic Disruptors

Dinitroanilines, such as Isopropalin: 4-isopropyl-2,6-dinitro-N,N-dipropylaniline Oryzalin: 3,5-dinitro-$N^4N^4$-dipropylsulfanilamide (I)

Pendimethalin: N-(1-ethylpropyl)-2,6-dinitro-3,4-xylidine

Prodiamine: 5-dipropylamino-a,a,a-trifluoro-4,6-dinitro-o-toluidine; 2,6-dinitro-$N^1N^1$-dipropyl-4-trifluoromethyl-m-phenylenediamine Trifluralin: a,a,a-trifluoro-2,6-dinitro-N,N-dipropyl-p-toluidine (I)

Inibitors of Amino Acid Synthesis

Glyphosate: N-(phosphonomethyl)glycine (I)

Sulfonylureas, such as Bensulfuron: a-(4,6-dimethoxypyrimidin-2-ylcarbamoylsulfamoyl)-o-toluic acid Chlorimuron: 2-(4-chloro-6-methoxypyrimidin-2-ylcarbamoylsulfamoyl)benzoic acid Chlorsulfuron: 1-(2-chlorophenylsulfonyl)-3-(4-methoxy-6-methyl-1,3,5-triazin-2-yl)urea Metsulfuron: 2-(4-methoxy-6-methyl-1,3,5-triazin-2-ylcarbamoylsulfamoyl)benzoic acid Nicosulfuron: 2-(4,6-dimethoxypyrimidin-2-ylcarbamoylsulfamoyl)-N,N-dimethylnicotinamide; 1-(4,6-dimethoxypyrimidin-yl)-3-(3-dimethylcarbamoyl-2-pyridylsulfonyl)urea Primisulfuron: 2-(4,6-bis(difluoromethoxy)pyrimidin-2-ylcarbamoylsulfamoyl)benzoic acid Sulfometuron: 2-(4,6-dimethylpyrimidin-2-ylcarbamoylsulfamoyl)benzoic acid; 2-(3-(4,6-dimethylpyrimidin-2yl)ureidosulfonyl)benzoic acid Thifensulfuron: 3-(4-methoxy-6-methyl-1,3,5-triazin-2-ylcarbamoylsulfamoyl)thiophen-2-carboxylic acid Triasulfuron: 1-(2-(2-chloroethoxy)phenylsulfonyl)-3(4-methoxy-6-methyl-1,3,5-triazin-2 yl)urea Tribenuron: 2-(4-methoxy-6-methyl-1,3,5-triazin-2-yl(methyl)carbamoylsulfamoyl)benzoic acid Imidazolinones, such as Imazamethabenz: a reaction product comprising(±)-6-(4-isopropyl-4-methyl-5-oxo-2-imidazolin-2-yl)-m-toluic acid (i) and (±)-2-(4-isopropyl-4-methyl-5-oxo-2-imidazolin-2-yl)-p-toluic acid (ii)

Imazapyr: 2-(4-isopropyl-4-methyl-5-oxo-2-imidazolin-2-yl)nicotinic acid

Imazaquin: (RS)-2-(4-isopropyl-4-methyl-5-oxo-2-imidazolin-2-yl)quinoline-3-carboxylic acid Imazethapyr: (RS)-5-ethyl-2-(4-isopropyl-4-methyl-5-oxo-2-imidazolin-2-yl)nicotinic acid

Inhibitors of Lipid Biosynthesis

Clethodim: (±)-2-[(E)-3-chloroallyloxyimino]propyl-5(2-(ethylthio)-propyl)-3-hydroxycyclohex-2-enone Diclofop-methyl: (RS)-2-(4-(2,4-dichlorophenoxy)phenoxy)propionic acid Fenoxaprop-ethyl: (±)-2-(4-(6-chloro-1,3-benzoxazol-2-yloxy)phenoxy)propionic acid; (±)-2-(4-(6-chlorobenzoxazol-2-yloxy)phenoxy)propionic acid Fluazifop-P-butyl: (R)-2-(4-(5-trifluoromethyl-2-pyridyloxy)phenoxy)propionic acid Haloxyfop-methyl: (RS)-2-(4-(3-chloro-5-trifluoromethyl-2-pyridyloxy)phenoxy)propionic acid Quizalofop: (RS)-2(4-(6-chloroquinoxalin-2-yloxy)phenoxy)propionic acid Sethoxydim: (±)-(EZ)-2-(1-ethoxyiminobutyl)-5-(2-(ehtylthio)propyl)-3-hydroxycyclohex-2-enone

Cell Wall Inhibitors

Dichlobenil: 2,6-dichlorobenzonitrile (I)

Isoxaben: N-(3-(1-ethyl-1-methylpropyl)-1,2-oxazol-5-yl)-2,6-dimethoxybenzamide; N((3-(1-ethyl-1-methylpropyl))isoxazol-5-yl)-2,6-dimethoxybenzamide

Cell Membrane Disruptors

Bipyridylium compounds, such as Diquat: 9,10-dihydro-8a-diazoniaphenanthrene; 6,7-dihydrodipyrido(1,2-a:2',1'-c)pyrazine-5,8-dium; 1,1'-ethylene-2,2'-bipyridyldiylium Paraquat: 1,1'-dimethyl-4,4'-bipyridinium (I)

Diphenylethers, such as Acifluorfen: 5-(2-chloro-a,a,a-trifluro-p-tolyoxy)-2-nitrobenzoic acid Fomesafen: [-(2-chloro-a,a,a-trifluro-p-tolyloxy)-N-mesyl-2-nitrobenzamide; 5-(2-chloro-a,a,a-trifluoro-p-tolyoxy)-N-methylsulfonyl-2-nitrobenzamide Lactofen: ethyl O-(5-(2-chloro-a,a,a-trifluoro-p-tolyloxy)-2-nitrobenzoyl)-DL-lactate Oxyfluorfen: 2-chloro-a,a,a-trifluoro-p-tolyl 3-ethoxy-4-nitrophenyl ether

Other Herbicides

Glufosinate: 4-(hydroxy(methyl)phosphinoyl)-DL-homoalaine; DL-homoalanin-4-yl-(methyl)phosphinic acid Bromoxynil: 3,5-dibromo-4-hydroxybenzonitrile (I); 3,5-dibromo-4-hydroxyphenyl cyanide; for ester, 2,6-dibromo-4-cyanophenyl octanoate (II).

EXAMPLES

The following examples are presented to further illustrate and explain the present invention and should not be taken as limiting in any regard. Unless otherwise indicated, all parts and percentages are by weight, and are based on the weight at the particular stage of the processing being described.

Example 1

The preparation of alkyl-modified silicones are described in this example. The SiH intermediates are prepared by acid equilibration as outlined in *Silicones, Chemistry and Technology* (CRC Press, 1991, pages 1 to 6, and U.S. Pat. No. 5,145,879 to Budnick, et al.).

The intermediates are then used to prepare a number of alkyl-modified silicones. A reaction vessel containing 777.0 g (2.81 moles) of an SiH intermediate (Me$_3$SiO[MeSi(H)O]$_{1.9}$SiMe$_3$) and 36.0 g (0.321 moles) 1-octene is heated to 90° C. while under a nitrogen blanket. The reaction is catalyzed with 2.25 mL of chloroplatinic acid (1.0% in ethanol), yielding 15 ppm chloroplatinic acid, based on the total charge. The reaction mixture exotherm is maintained between 100° and 115° C. while the remaining 668.0 g (6.14 moles) 1-octene was added dropwise. The reaction mixture is allowed to stir at 100° C. for two hours after the addition of the olefin is complete. The product shows no traces of SiH when introduced to a fermentation tube containing KOH/water/ethanol solution. The product is filtered, and stripped on a Rotovap at 70° C./≦5 mm Hg for 2 hours. The resulting product is a clear amber liquid with a Brookfield (spindle LV-3) viscosity of 20 cps at 25° C., shown as AMS-2 in Table 1.

Using this procedure, various alkyl-modified silicones (AMS) of the general structure

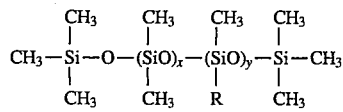

wherein the values for x, y, and R, the type of alkyl contained in the AMS, are varied as listed in Table 1 below.

TABLE 1

Structures of Alkyl-Modified Silicones

| Compound | X | Y | Alkyl (R) | % Alkyl |
|---|---|---|---|---|
| AMS-1 | 0 | 1 | C$_8$ | 33.5 |
| AMS-2 | 0 | 1.9 | C$_8$ | 43.5 |
| AMS-3 | 0 | 1 | C$_{12}$ | 43.1 |
| AMS-4 | 5 | 7 | C$_8$ | 45.1 |
| AMS-5 | 5 | 7 | C$_{12}$ | 55.2 |
| AMS-6 | 5 | 10 | C$_8$ | 49.7 |
| AMS-7 | 5 | 10 | C$_{12}$ | 59.7 |
| AMS-8 | 7 | 3 | C$_8$ | 28.1 |
| AMS-9 | 7 | 3 | C$_{12}$ | 36.9 |
| AMS-10 | 10 | 10 | C$_8$ | 42.7 |
| AMS-11 | 1 | 1 | C$_8$ | 27.4 |
| AMS-12 | 7 | 3 | C$_{14}$ | 40.6 |
| AMS-13 | 0 | 1 | C$_{14}$ | 46.9 |
| AMS-14[a] | 2 | 2 | C$_8$ | 45.5 |
| AMS-15 | 18 | 4.5 | C$_8$ | 22.2 |
| AMS-A | 80 | 8 | C$_8$ | 12.0 |
| AMS-B | 50 | 30 | C$_{10}$ | 42.6 |
| AMS-C | 120 | 40 | C$_{12}$ | 37.0 | a. AMS-14 is based on a cyclic siloxane of the nominal structure D$_2$D*$_2$, where D = Me$_2$SiO and D* = MeSi(R)O with R = C$_8$ alkyl.

As comparative examples, polyoxyalkyleneoxide silicone copolymers having the formula

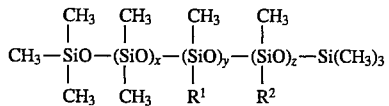

are prepared as described in U.S. Pat. Nos. 2,834,748 and 3,507,815, and the CRC *Silicones* book cited above at pages 114 to 115, with values for the structural variables of the compounds as outlined in Table 2 below.

TABLE 2

| | Variables for Comparative Structures | | | | |
|---|---|---|---|---|---|
| Cmpd | x | y | z | pendant group | % alkyl |
| SIL-A | 0 | 1 | 0 | R$^2$ = C$_3$H$_6$O(CH$_2$CH(CH$_3$)O)$_4$H | 0 |
| SIL-B | 0 | 1 | 0 | R$^2$ = C$_3$H$_6$O((CH$_2$CH(CH$_3$)O)$_{13}$C$_4$H$_9$ | 0 |
| SIL-C | 5 | 5 | 5 | R$^1$ = CH$_2$(CH$_2$)$_6$CH$_3$ R$^2$ = C$_3$H$_6$O(CH$_2$CH$_2$O)$_8$CH$_3$ | |

TABLE 2-continued

Variables for Comparative Structures

| Cmpd | x | y | z | pendant group | % alkyl |
|------|---|---|---|---------------|---------|
| SIL-D | 5 | 5 | 5 | $R^1 = CH_2(CH_2)_{10}CH_3$<br>$R^2 = CP_3H_6O(CH_2CH_2O)_8CH_3$ | 20.5 |

Example 2

This example demonstrates the solubility of the AMS silicones prepared in Example 1 in mineral oil and in a variety of vegetable oils, compared to the polyalkyleneoxide-modified silicones (denoted SIL-A and SIL-B) and polyalkyl-polyalkyleneoxide silicones (denoted SIL-C and SIL-D) prepared in Example 1.

The solubilities of the AMS samples and the comparative samples are examined by making a 1:1 mixture of the silicone with each of the following carrier oils: mineral oil (denoted A in the Table below, a white mineral oil obtained from Gloria, Witco Corp., 520 Madison Ave., NY, N.Y. 10022-4236 having a viscosity of 39–42 cSt at 40° C.; SP6=0.859–0.880 at 25° C.), methylated soybean oil (denoted B below, obtained from Henkel Canada, Limited, 2290 Argentina Rd., Mississauba, Ontario L5N 6H9, and soybean oil (denoted C). Solubility in all three oils is observed for the AMS compounds having degree of polymerization (DP) of ≦6, and an alkyl content of ≦50 Wt % (Table 3). The DP is defined as the total value of x+y+2 (the number of siloxane units in the silicone copolymer plus two end groups), as described in Table 1. The obvious exception is AMS-14, which is a cyclic structure, and therefore the DP=x+y.

TABLE 3

Solubility of Alkyl-Modified Silicones in Carrier Oils.

| Cmpd | Alkyl | DP | % Alkyl | Oil A | Oil B | Oil C |
|------|-------|-----|---------|-------|-------|-------|
| AMS-1 | $C_8$ | 3 | 33.5 | S | S | S |
| AMS-2 | $C_8$ | 3.9 | 43.5 | S | S | S |
| AMS-3 | $C_{12}$ | 3 | 43.1 | S | S | S |
| AMS-4 | $C_8$ | 14 | 45.1 | S | S | I |
| AMS-5 | $C_{12}$ | 4 | 55.2 | S | S | I |
| AMS-6 | $C_8$ | 17 | 49.7 | S | S | I |
| AMS-7 | $C_{12}$ | 17 | 59.7 | S | S | I |
| AMS-8 | $C_8$ | 12 | 28.1 | S | S | I |
| AMS-9 | $C_{12}$ | 12 | 36.9 | S | S | I |
| AMS-10 | $C_8$ | 22 | 42.7 | S | S | I |
| AMS-11 | $C_8$ | 4 | 27.4 | S | S | S |
| AMS-12 | $C_{14}$ | 12 | 40.6 | S | S | I |
| AMS-13 | $C_{14}$ | 3 | 46.9 | S | S | S |
| AMS-14 | $C_8$ | 4 | 45.5 | S | S | S |
| AMS-15 | $C_8$ | 24.5 | 22.2 | S | S | I |
| AMS-A | $C_8$ | 90 | 12.0 | I | I | I |
| AMS-B | $C_{10}$ | 82 | 42.6 | S | S | I |
| AMS-C | $C_{12}$ | 162 | 37.0 | S | S | I |
| SIL-A | N/A | 3 | N/A | S | S | S |
| SIL-B | N/A | 3 | N/A | I | S | S |
| SIL-C | $C_8$ | 17 | 14.7 | I | S | S |
| SIL-D | $C_{12}$ | 17 | 20.5 | I | S | S |

Similar solubility results are expected for canola oil, castor oil, palm oil, safflower oil, and methylated vegetable oils. For example, AMS-1 in a 1:1 mixture is soluble in both canola oil and safflower oil.

Example 3

The AMS component must be dispersible or soluble in the hydrocarbon oil or vegetable oil matrix in order to be effective at reducing surface tension. This example demonstrates that the AMS component reduces the surface tension of carrier oils, such as soybean oil, to a greater extent than oil-soluble polyalkyleneoxide-modified silicones (denoted SIL-A in the table below). The surface tension of silicone/oil blends is measured by the Wilhelmy plate method (25° C.), using a sand-blasted platinum blade as the sensor, to obtain values set out in Table 4 below.

TABLE 4

Surface Tension of AMS versus Comparative Silicones in Soybean Oil

| WT % AMS | AMS-1 | AMS-3 | SIL-A | SIL-B |
|----------|-------|-------|-------|-------|
| 0 | 33.9 | 33.9 | 33.9 | 33.9 |
| 1 | 32.1 | 34.2 | 33.4 | 34.2 |
| 5 | 28.4 | 27.4 | 31.5 | 33.9 |
| 10 | 27.7 | 28.5 | 30.1 | 33.2 |
| 25 | 25.6 | 27.7 | — | 32.9 |
| 50 | 23.3 | 22.2 | 25.6 | 31.0 |
| 100 | 22.1 | 24.3 | 24.2 | 31.4 |

The AMS's of the invention are also effective at reducing the surface tension of other oils, such as mineral oil and methylated soybean oil, as illustrated in Table 5 below.

Example 4

The spreading performance of compositions of the invention is evaluated in this example. Spreading is determined by applying a 10 μL drop of the silicone oil on a morningglory leaf (*Ipomeoa hederacea*) using a micropipette, and measuring the spread diameter after 1 minute with a ruler. The following spread rating is used to describe the degree of spreading:

1=≧2 mm but ≦5 mm

2=>5 mm but ≦10 mm

3=>10 mm but ≦20 mm

4=>20 mm but ≦30 mm

5=>30 mm

Data are compared to control oil A, mineral oil (Gloria); oil B, methylated Soybean Oil (Emery); and oil C, soybean oil, as tablulated in Table 6 below.

TABLE 5

Surface tension of AMS vs Comparative Silicones in Various Oils.

| ADDITIVE | MINERAL OIL | METHYL SOYATE |
|---|---|---|
| NONE | 32.8 | 31.8 |
| AMS-1 | 24.7 | 24.2 |
| AMS-2 | 24.8 | 24.8 |
| AMS-4 | 24.6 | 25.1 |
| AMS-8 | 23.0 | 24.5 |
| AMS-10 | 26.3 | 28.1 |
| AMS-11 | 24.5 | 24.8 |
| AMS-12 | 26.1 | 26.3 |
| AMS-13 | 25.1 | 25.4 |
| AMS-14 | 24.5 | — |
| AMS-B | 27.8 | — |
| AMS-C | 26.8 | 27.3 |
| SIL-C | — | 30.9 |

The AMS spreading ability is influenced by the chain length of the alkyl, as evidenced by comparing the spreading of AMS-1, AMS-3, and AMS-13. All three compounds have the same trisiloxane backbone and differ only in the alkyl moiety. The degree of spreading decreases with an increase in the chain length from $C_8$ to $C_{14}$. Similar results are observed for the other AMS pairs (AMS-4/AMS-5; AMS-6/AMS-7, etc.).

All of the oil-soluble AMS structures (with the exception of AMS-10) having a DP of $\leq 25$ (see Table 3 for DP) and having an alkyl content of $\leq 50$ weight %, give an increase in the spread diameter relative to the polyalkyleneoxide silicones and conventional oil carriers used here as comparative examples. The greatest degree of spreading is obtained with the AMS components having a DP of $\leq 4$.

TABLE 6

Spreading of Alkyl-Modified Silicones on Morningglory.

| Compound | Alkyl | % Alkyl | Spread Factor |
|---|---|---|---|
| AMS-1 | $C_8$ | 33.5 | 5 |
| AMS-2 | $C_8$ | 43.5 | 4 |
| AMS-3 | $C_{12}$ | 43.1 | 3 |
| AMS-4 | $C_8$ | 45.1 | 2 |
| AMS-5 | $C_{12}$ | 55.2 | 1 |
| AMS-6 | $C_8$ | 49.7 | 2 |
| AMS-7 | $C_{12}$ | 59.7 | 1 |
| AMS-8 | $C_8$ | 28.1 | 3 |
| AMS-9 | $C_{12}$ | 36.9 | 2 |
| AMS-10 | $C_8$ | 42.7 | 1 |
| AMS-11 | $C_8$ | 27.4 | 5 |
| AMS-12 | $C_{14}$ | 40.6 | 2 |
| AMS-13 | $C_{14}$ | 46.9 | 2 |
| AMS-14 | $C_8$ | 45.5 | 3 |
| AMS-15 | $C_8$ | 22.2 | 2 |
| AMS-A | $C_8$ | 12.0 | 2 |
| AMS-B | $C_{10}$ | 42.6 | 1 |
| AMS-C | $C_{12}$ | 37.0 | 1 |
| SIL-A | N/A | N/A | 2 |
| SIL-B | N/A | N/A | 1 |
| SIL-C | $C_8$ | 14.7 | 1 |
| SIL-D | $C_{12}$ | 20.5 | 1 |
| OIL A | N/A | N/A | 1 |
| OIL B | N/A | N/A | 1 |
| OIL C | N/A | N/A | 1 |

Example 5

The ability of the AMS compounds to promote spreading of the oil carrier on a leaf surface is demonstrated in this example. AMS/oil blends are prepared in a 1:1 ratio by weighing equal amounts of material into a 2 dram vial. The components are shaken to provide a homogeneous mixture. The oil carriers consisted of mineral oil or methylated soybean oil. Spreading is evaluated on AMS/oil combinations, where the AMS is soluble in the oil carrier.

A 10 μL drop of the AMS/Oil mixture is applied to freshly excised leaf and allowed to spread for 2 minutes. Velvetleaf (*Abutilon theophrasti*) at the 7- to 8-leaf stage was used as the test surface. The spread diameter of the droplet is measured using a digital caliper (Max-Cal, Fowler & NSK). Results are tablulated in Table 7 below. (Denotations in the Table are ND=not determined; N/A=not applicable).

TABLE 7

| Spreading Ability of AMS/Oil Blends on Velvetleaf. | | | | |
|---|---|---|---|---|
| | | | SPREAD DIAMETER (mm) | |
| Compound | Alkyl | % Alkyl | Mineral Oil | Methyl Soyate |
| AMS-1 | $C_8$ | 33.5 | 20.2 | 22.3 |
| AMS-2 | $C_8$ | 43.5 | 8.7 | 7.8 |
| AMS-3 | $C_{12}$ | 43.1 | 7.9 | 7.9 |
| AMS-4 | $C_8$ | 45.1 | 10.8 | 6.9 |
| AMS-5 | $C_{12}$ | 55.2 | 7.2 | ND |
| AMS-8 | $C_8$ | 28.1 | 10.8 | 8.0 |
| AMS-9 | $C_{12}$ | 36.9 | 7.7 | ND |
| AMS-10 | $C_8$ | 42.7 | 6.8 | 6.2 |
| AMS-11 | $C_8$ | 27.4 | 20.5 | 24.1 |
| AMS-13 | $C_{14}$ | 46.9 | 16.8 | 11.5 |
| AMS-14 | $C_8$ | 45.5 | 19.6 | ND |
| AMS-B | $C_{10}$ | 42.6 | 6.4 | ND |
| AMS-C | $C_{12}$ | 37.0 | 4.7 | 5.9 |
| SIL-A | N/A | N/A | ND | 6.6 |
| NONE | N/A | N/A | 4.8 | 4.9 |

The data show that in all cases the addition of an AMS component of the present invention to the oil carrier increases the spread diameter of the oil droplet relative to the carrier oil alone.

Table 8 illustrates the effect of the AMS concentration on the spreading of Sunspray® oil (Mycogen) on pea leaf. A 0.5 μL droplet of the AMS/Sunspray oil mixture is applied to the leaf surface and the spread diameter is measured at 6 minutes after application.

TABLE 8

| Spreading Ability of AMS/Sunspray ® Oil Blends. | | |
|---|---|---|
| | SPREAD AREA ($mm^2$) | |
| Weight % AMS | AMS-1 | AMS-2 |
| 0 | 48 | 48 |
| 5 | 86 | 74 |
| 10 | — | 78 |
| 20 | 92 | 85 |
| 40 | — | 107 |
| 60 | — | 132 |

Sunspray® oil alone spreads to 48 $mm^2$. It can be seen that the inclusion of the AMS component in Sunspray® oil, even at a level of 5%, significantly increases the spread area relative to Sunspray® oil alone (0% silicone).

Example 7

This example demonstrates that crop oil concentrate (COC) formulations containing an AMS component, an oil carrier, a hydrophobized filler such as silica, and a nonionic surfactant provide a low-foam composition relative to a formulation without the AMS component. Table 9 gives the components of the COC formulations. The COC formulations are prepared by combining the components in a 1 ounce jar and mixing by hand with a spatula for 3 minutes. Each of the COC's are prepared as 1 wt % dispersions in distilled water (total=50 mL). The bottles are shaken on a wrist action shaker for 10 minutes. The foam height after a 10-minute shake was measured using a ruler. In addition, the foam collapse time is measured for the existing foam.

TABLE 9

| Crop Oil Concentrate Formulations | | | | |
|---|---|---|---|---|
| Compound | COC-1 | COC-2 | COC-3 | COC-4 |
| MINERAL OIL | 43.3 | 60.7 | 55.7 | 68.3 |
| SILICA/OIL BLEND[a] | 21.7 | 4.3 | 9.3 | 21.7 |
| AMS-1 | 25.0 | 25.0 | 25.0 | 0 |
| TERGITOL ® 15-S-7 | 10.0 | 10.0 | 10.0 | 10.0 |
| Wt % Silica Contained in COC | 1.25 | 0.25 | 0.54 | 1.25 |

[a]The silica (Tullanox ® 500) is prepared in a masterbatch at 5.77 wt % in mineral oil.

Table 10 demonstrates that the COC's containing the AMS component and the silica filler give a greater degree of foam control than the COC formulation prepared without the AMS component. Also, good foam control is achieved at very low levels of silica filler.

TABLE 10

| Effect of AMS Component on Foam Control. | | |
|---|---|---|
| COC Formulation | mL Foam | Collapse Time (sec.) |
| COC-1 | 0 | $\leq 1$ |
| COC-2 | 0 | $\leq 1$ |
| COC-3 | 0 | $\leq 1$ |
| COC-A | 6 | $\geq 60$ |

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention as defined in the appended claims. The claims are intended to cover the claimed components and steps in any sequence which is effective to meet the objectives there intended, unless the context specifically indicates the contrary.

We claim:

1. An agricultural composition comprising from about 1% to about 99% by weight of an oil and from about 99% to about 1% by weight of an organosilicone of the formula:

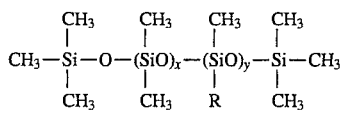

wherein x=0 to 10, y=1 to 5, and R is an alkyl or alkyl ester group containing 8 to 12 carbons wherein the organosilicone has an alkyl content of less than or equal to fifty percent by weight and has a degree of polymerization of less than or equal to 12.

2. A composition according to claim 1 wherein the organosilicone compound has a degree of polymerization of $\leq 6$.

3. A composition according to claim 1 comprising a compound having x=0 to 1 and y=1.

4. A composition according to claim 1 further comprising from about 1% to about 50% by weight of a nonionic surfactant that is soluble in the alkyl silicone/oil composition and has an HLB between 8 and 17.

5. A composition according to claim 1 further comprising from about 0.1% to about 2.5% by weight of a hydrophobized silica filler.

* * * * *